US00PP14389P29

(12) United States Plant Patent
Snyder

(10) Patent No.: US PP14,389 P2
(45) Date of Patent: Dec. 16, 2003

(54) BEGONIA PLANT NAMED 'STAR OF DAVID'

(50) Latin Name: *Begonia rex*
Varietal Denomination: Star of David

(76) Inventor: David W. Snyder, 34139 Radio Rd., Leesburg, FL (US) 34139

( * ) Notice: Subject to any disclaimer, the term of this patent is extended or adjusted under 35 U.S.C. 154(b) by 50 days.

(21) Appl. No.: 10/020,788

(22) Filed: Dec. 14, 2001

(51) Int. Cl.[7] ..... A01H 5/00
(52) U.S. Cl. ..... Plt./343
(58) Field of Search ..... Plt./343, 348

(56) References Cited

U.S. PATENT DOCUMENTS

PP12,598 P2 * 4/2002 Koppe ..... Plt./348

* cited by examiner

*Primary Examiner*—Kent Bell
(74) *Attorney, Agent, or Firm*—Allen, Dyer, Doppelt, Milbrath & Gilchrist, P.A.

(57) ABSTRACT

A new and distinct cultivar of Begonia rex plant, named 'Star of David', characterized by its juvenile flowers being a mutation with large, forty-flower clusters, resistance to disease, insects, and dampness, improved resistance to cold, and possessing a year-round duration of the flowering season.

4 Drawing Sheets

Variety denomination: The present invention relates to a new and distinct cultivar of Begonia rex plant botanically known as Begonia rex hybrid, referred to by the name of 'Star of David'.

BACKGROUND OF THE INVENTION

The new Begonia rex was discovered and selected by the Inventor in a controlled environment in Oviedo, Fla., in 1998, and is at present growing in a controlled environment in Leesburg, Fla.

The Inventor has been growing a Begonia he collected in Venezuela in 1983. That plant is not known by the Inventor to be patented, nor is it known to be the subject of a pending U.S. patent application. In 1998 the Inventor noticed a sport on the original cultivar, consisting of a single stem that developed significantly larger flower clusters. The clusters on this stem routinely contained forty or more flowers, compared with the six to eight normally produced by the original parent plant that had been collected. The Inventor selectively propagated the stem (sport) by vegetative stem cuttings. The sport was discovered and propagated at 5344 Rockinghorse Place, Oviedo, Fla. 32765. All the resulting plants have maintained the large flower clusters like the original sport. The Inventor has been privately propagating and evaluating the inventive plant for 4–5 years. The Inventor has in that time determined that the improved traits were stable, the instant plant retaining its distinctive characteristics and reproducing true to type in successive generations.

The parent cultivar may be described as follows:

Flowers: 10–14 flowers per cyme (female) and 4–6 flowers per cyme (male), with 2–3 cymes per adult plant. Adult and juvenile plants had the same small number of flowers per cyme. Perennial; 2–3 cymes per plant per year for many years observed.

Plant form: Upright and mounding, with stems of 1-cm width at one year.

Branching: Mostly upright, with stem supports added as needed.

Growth habit: Slow 10–12 in./in. to maturity in 6 mo in 3-gallon container; 24 in./year.

Disease and pest resistance: No diseases nor root rot ever observed. Insects not attracted.

Cold resistance: Cover needed at temperatures below 32° F.

RELATED ART

As described in (W. B. Zomlefer, *Guide to Flowering Plant Families,* Univ. North Carolina Press, Chapel Hill, N.C., 1994, p. 124; A. Huxley, ed., *New Royal Horticultural Society Dictionary of Gardening,* Vol. 4, Macmillan, London, 1992), the Begonia (Begoniaceae) comprises 900+ species of usually succulent herbs, shrubs, or climbers. There are more than 100 species and 10,000 hybrids and cultivars of Begonia cultivated as ornamentals grown for attractive foliage and flowers.

Begonia roots are fibrous, rhizomatous, or tuberous, with the tubers becoming dormant in the winter. The stems are often swollen, conspicuously jointed, and woody, extending up to 2 m and above. Alternatively, the stems may be soft and herbaceous, or absent, with the leaves forming a rosette at the apex of the rhizome.

Begonia leaves are alternate and petiolate, and are usually asymmetric, with one side shorter than the other, resembling an elephant's ear. The leaves may be simple to lobed, or occasionally compound, having a margin that is irregularly toothed, glabrous to hispid, with a surface smooth to rugose or bullate, membranous to coriaceous, often brightly marked red, purple, brown, grey, to white.

There are two stipules, often large, membranous, often persistent, sometimes caducous. Inflorescence comprises an axillary or terminal cyme or raceme, erect or pendent, with few to many flowers present. The flowers are unisexual, with male and female adjacent in inflorescence. The flowers are sometimes dimorphic in size, with colors comprising red, pink, white, and yellow to orange, and may be bicolored and double in cultivation.

The corolla segments (tepals) are 2+2 in male flowers and 2–6 in females; they are of different sizes but are similarly colored. They are sometimes hairy externally, glabrous in the inner surface, waxy in texture, and of crystalline appearance. The stamens are numerous, massed at the center, or connate below, forming a tube, with yellow anthers. The ovary is inferior, 3–4 locular, many ovules, three styles, and free or connate below. The stigmata are lobed and convolute, or capitate. The fruit is a loculicidal capsule, usually winged. The seeds are very numerous, minute, and oblong. The plants reproduce vegetatively from groups of small tubers, often found in the leaf axils, or by adventitious buds that readily form on detached leaves in contact with moist soil. The buds arise on the upper leaf surface from a meristem that develops within the callus formed over the wound.

The begonia is typically found in the tropics and subtropics, in damp, wooded areas, especially in the Americas, with most diversity in South America. In the United States and Canada, there are two spp. of Begonia.

The majority of species in cultivation are grown as potplants, using a free-draining peat-based potting medium with a pH of 6.0–7.0 and with at least some shade from direct sunlight. Most begonias are frost tender.

SUMMARY OF THE INVENTION

The present invention, the 'Star of David' Begonia rex cultivar, is a new Begonia variety that is disease-resistant, resists root rot, tolerates freezes, is a perennial, and does not attract insects.

BRIEF DESCRIPTION OF THE DRAWINGS

The accompanying colored photographs illustrate the overall appearance of the new Begonia, showing the colors as true as it is reasonably possible to obtain in colored reproductions of this type. Colors in the photographs differ slightly from the color values cited in the detailed botanical description, which accurately describes the colors of the new Begonia.

The photograph on the first sheet comprises a side perspective view of a typical juvenile, 8-wk-old plant in a 1-gal container. The large, mature flowers are beginning to open.

On the second sheet are depicted typical leaves, showing, top to bottom, a new leaf, bottom and top sides of a mature leaf, approximately 6 in. long, and top and bottom sides of a juvenile leaf.

The photographs on the third and the fourth sheets comprise side perspective views of a mature flower cluster.

DETAILED BOTANICAL DESCRIPTION

A description of the Begonia variety of the present invention will now be presented. Color references are made to The Royal Horticultural Society Colour Chart, except where general terms of ordinary dictionary significance are used. Except as noted, data are from approximately 10-week-old plants growing in a 1-gal container.

Botanical classification: Begonia rex hybrid.
Commercial classification: Rex Begonia.
Parentage: Stem selection of Begonia rex hybrid.
Propagation:

*Type.*—Stem cuttings.

*Time to initiate roots.*—Approximately 21–26 days year round.

*Root description.*—Fine, fibrous, and well-branched.

*Characterization.*—Vigorous and rapid growth.

*Seed production.*—Seed production has not been observed.

Plant description:

*Plant form.*—Upright and mounding stems of approximately 2 cm width at one year in a 3-gal container. Branching: Upright with horizontally extending branches, giving fullness to plant.

*Growth habit.*—Vigorous growth rate to a height of 3–4 ft in 8 mo, and to a height of 5–6 ft in 1.5 yr. Growth in 3-gal container from 6-in. cuttings. Tolerates temperatures down to 32° F.; cover below 32° F.

*Plant height.*—Approximately 150 cm at one year (3-gal container).

*Plant width.*—Approximately 90 cm at one year (3-gal container).

*Leaves.*—Length: About 15 cm. Width: About 7 cm. Shape: Asymmetrical. Apex: Oblate. Base: Oblique. Margin: Slightly undulating, entire. Texture: Smooth. Petiole length: About 1–1.5 cm. Color, young, fully expanded leaves (in 1-gal container at 10 weeks): Upper surface: 137A. Lower surface: 137C. Venation: 137A, upper side; 137C, lower side. Petiole: Upper: 45A. Lower: 148B to 148C. Color, juvenile new leaves: Upper surface: 144A. Lower surface: 147C.

*Stems.*—Color: 138A to 138B. Color of pale spots on stems: 193A to 193B.

Flower description:

*Flowering habit.*—Flowering continuous. Both juvenile and adult plants have clusters of approximately 40 flowers, with 10–25 cymes per adult plant. Filtered sunlight preferred. Time to first flowering is approximately 2–3 weeks from a rooted cutting. Individual blooms last approximately 4–5 weeks.

*Fragrance.*—None observed.

*Natural flowering season.*—Year round, Southern U.S. climate; April–September, Northern U.S. climate.

*Shape.*—Rounded. Diameter: About 2–3 cm. Depth (height): About 2.5–3 cm.

*Flower buds.*—Rounded. Length: About 1–2 cm. Diameter: About 0.5 cm. Color: 51C to 51D.

*Tepals.*—Size: Outer (large) tepals: Length: About 1.5 cm. Width: About 2.0 cm. Shape: Ovate. Apex: Obtuse. Base: Cordate. Margin: Entire. Texture: Appears smooth. Inner (small) tepals: Length: About 1.0 cm. Width: About 0.5 cm. Color: Fully opened, upper surface, 51C to 51D. Fully opened, lower surface, 51C to 51D. Shape: Elliptical. Apex: Obtuse. Base: Oblique. Margin: Entire. Texture: Appears smooth.

*Peduncles.*—Angle: 35–45°. Length: About 2.5–3 cm. Texture: Smooth. Color: 50A to 50B.

*Pedicels.*—Angle: Erect. Length: About 1.5 cm. Texture: Smooth. Color: 50A to 50B.

*Reproductive organs.*—Number of pistils: Six per flower. Pistil length: About 0.25 cm. Anthers color: 20A to 20B. Ovaries: Inferior, three-winged. Stigma color: 17A to 17B. Styles color: 17A to 17B. Pollen color: Small amounts of pollen observed by microscope, having color 155A/B.

Disease resistance: No diseases nor root rot since discovery and propagation. Insects not observed to be attracted. No experiments with exposure to diseases common to Begonia have been conducted.

The plant of the present invention comprises a spontaneously derived cultivar, possibly by selection. The present plant has evolved into a much stronger, fuller, horizontally branching flower via stem cuttings. The cuttings comprised only the strongest plants, leading to a stronger plant, which in turn was cut to form ever-stronger plants. This process was repeated over a 20-year time span to reach the plant having the characteristics shown and claimed herein, leading to a plant having improved horizontal fullness and branching and significantly enlarged flower bunches on both adult and juvenile plants. Fecundity may also be accomplished with leaf propagation as well as stem cuttings, and there is neither propagation through seeds nor root propagation.

The genus and species of the present invention are Begonia rex hybrid. The habit of growth comprises a fibrous-rooted, tuberous, semperflorens, rhizomatous, rex-cultorum species. The stems are thick and cane-bamboo-like and are green with numerous pale spots. The stems, which are multiple, grow to 5 cm in width and to 8 feet tall. The vigor is characterized as very strong, with an ever-flowering productivity. The precocity is characterized as reaching 5–6 feet tall in a growth period of 1–2 years.

The botanical characteristics of the plant structures may be characterized as follows: There are abundant, alternate leaves that are asymmetrically shaped, having an oblate apex and oblique base. The leaves are not hairy, and have one side shorter than the other with no spots. The undersides of the leaves are a dull, glossy, lighter green than the top sides, and the leaf margins are crenate. A typical leaf is about 15 cm long. The petiole is about 1.0–1.5 cm long.

The inflorescence is axillarily showy, dichotomously branching. The pedicels are dark rose. The female flowers are drooping, with three broad pink wings on the ovary. The pistil has 3 stigmata branches that are gold-yellow, while the five tepals are pale pink. The male flowers have two large outer tepals and two small inner tepals. The male has a cluster of bright gold stamens.

Other distinguishing characteristics over prior art begonias include resistance to disease, cold, and dampness, and a year-round duration of the flowering season. In addition, the flowers appear to be "shielded" by the leaves (see, for example, the first sheet of photographs), which is different from, for example, prior art begonias known to the present Inventor.

What is claimed is:

1. A new and distinct cultivar of Begonia plant named 'Star of David', as illustrated and described.

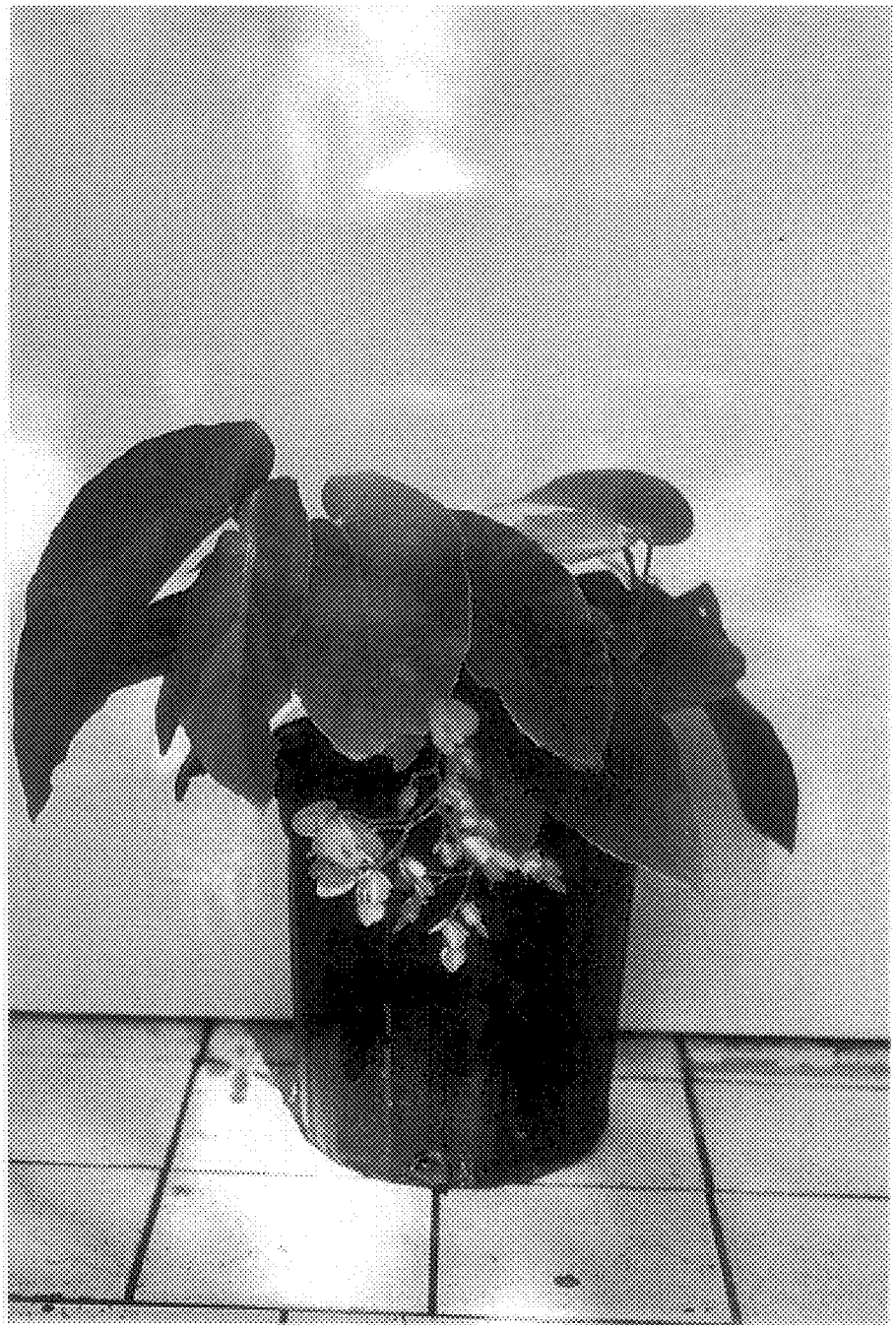

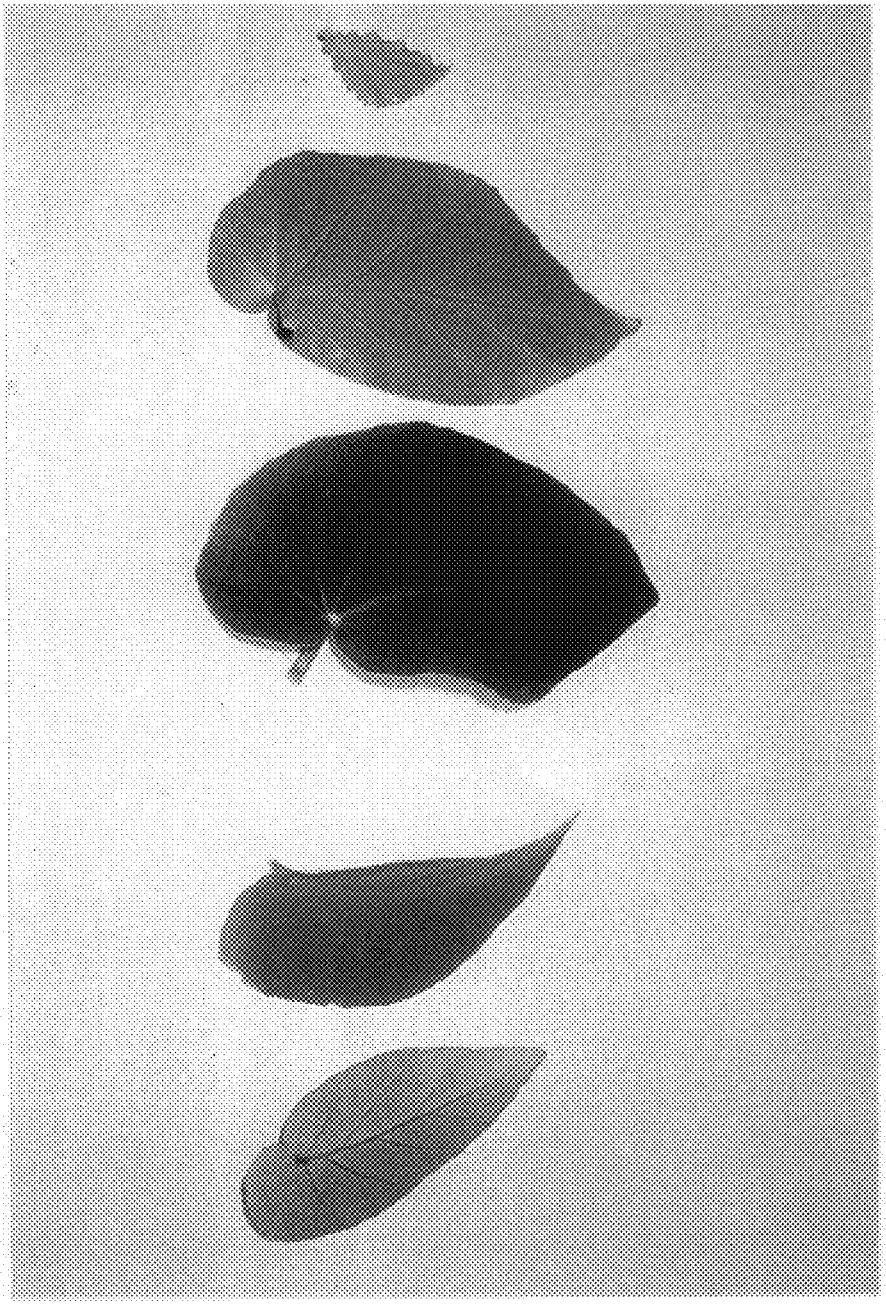

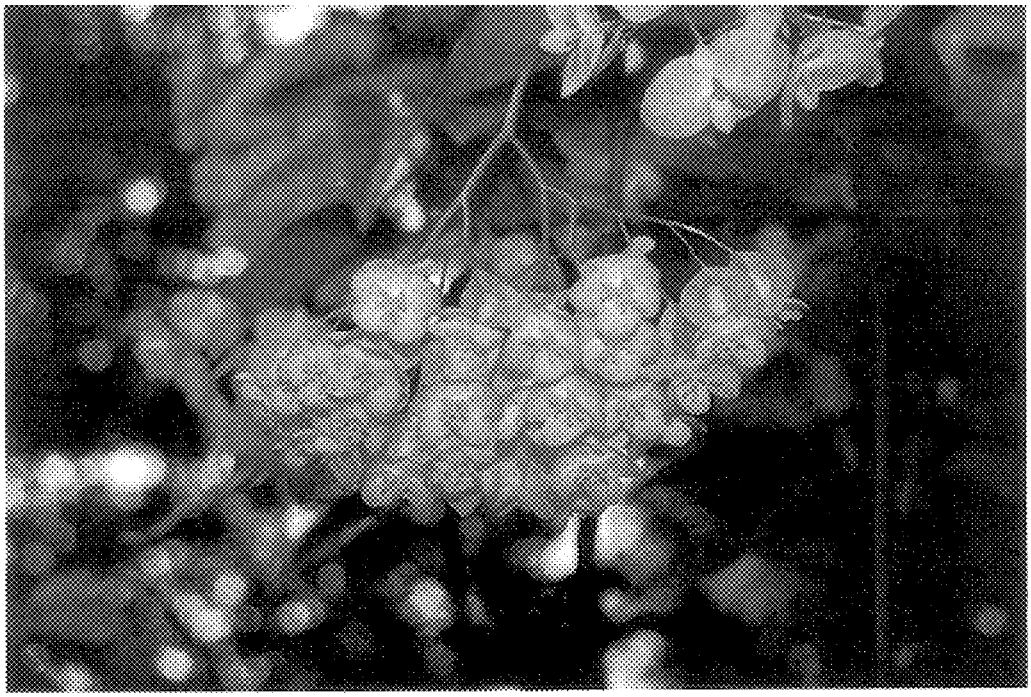

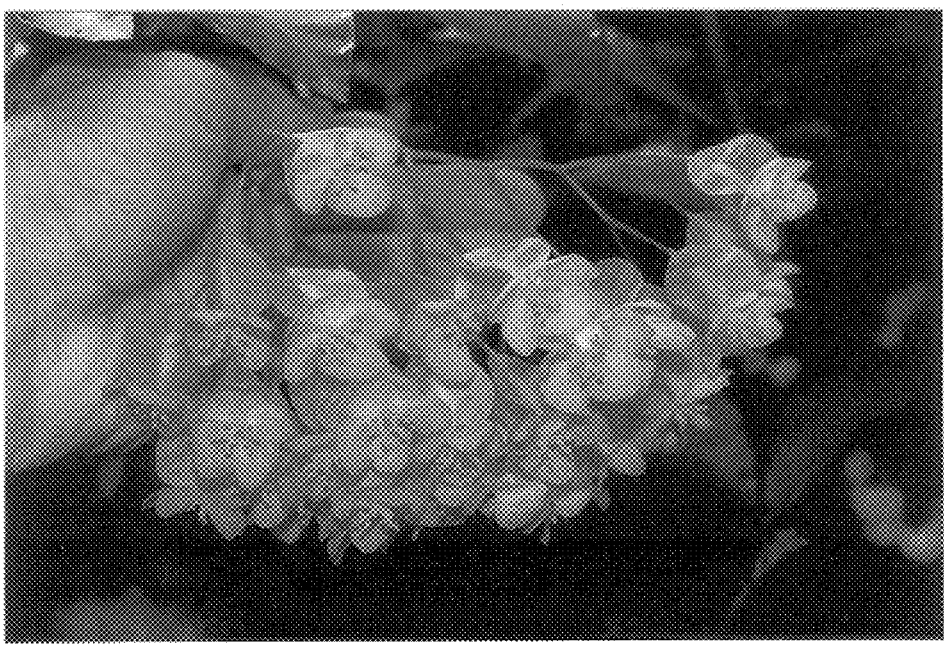

* * * * *